(12) United States Patent
Hendrick et al.

(10) Patent No.: US 6,337,068 B1
(45) Date of Patent: *Jan. 8, 2002

(54) LACTORBACILLUS BUCHNERI COMPOSITIONS FOR IMPROVING AEROBIC STABILITY OF SILAGE

(75) Inventors: Carol A. Hendrick, Des Moines, IA (US); Barbara G. Ruser, Buxtehude (DE); Cora R. Wortman, Ames; Scott M. Dennis, Urbandale, both of IA (US)

(73) Assignee: Pioneer Hi-Bred International, Inc., Des Moines, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 17 days.

(21) Appl. No.: 09/105,784

(22) Filed: Jun. 26, 1998

(51) Int. Cl.$^7$ .............................................. A01N 63/00
(52) U.S. Cl. .................................. 424/93.45; 435/252.1
(58) Field of Search ..................... 435/252.1; 424/93.45

(56) References Cited

U.S. PATENT DOCUMENTS 4,863,747 A    9/1989    Tomes

FOREIGN PATENT DOCUMENTS

| WO | 0311 469 A | 4/1989 | ............ C12N/15/00 |
| WO | WO 97/29644 | 8/1997 | ............ A23K/1/00 |
| WO | WO 97 29644 A | 8/1997 | |

OTHER PUBLICATIONS

Ranjit et al., "The effects of *Lactobacillus plantarum* (LP), *Lactobacillus buchneri* (LB) and a propionic acid–based preservative on the fermentation and aerobic stability of corn silage and the aerobic stability of a TMR", *J of Dairy Science*, 81(supp.1) 1998, p 196 (XP002119009).

Cooke, L., "New strain slows silage spoilage", *Agricultural Research*, 43(6) Jun. 1, 1995, p. 17 (XP002034342).

Weinberg, Z.G., "New trends and opportunities in the development and use of inoculants for silage", *FEMS Microbiology Reviews* 19(1966) 53–68.

Kitamoto, Hiroko K., "Selection of killer yeasts (*Kluyveromyces lactis*) to prevent aerobic deterioration in silage making", *J. Dairy Sci.* (1993) 76:803–811.

*Primary Examiner*—Irene Marx
(74) *Attorney, Agent, or Firm*—David B. Ran; Pioneer Hi-Bred International, Inc.; Heidi Nebel

(57) ABSTRACT

A method for treating silage to enhance aerobic stability by inhibiting growth of microorganisms selected from yeasts, molds and spore-forming bacteria is disclosed. The method comprises treating silage or feed with a composition comprising *Lactobacillus buchneri*, LN 3957, or the antimicrobial components produced thereby. According to the invention, a strain of Lactobacillus has been purified and isolated which is nontoxic, safe and which improves aerobic stability of silage.

29 Claims, 1 Drawing Sheet

LACTORBACILLUS BUCHNERI COMPOSITIONS FOR IMPROVING AEROBIC STABILITY OF SILAGE

FIELD OF THE INVENTION

This invention relates generally to the silage process and to microorganisms and use of the same in treating animal feed and silage to enhance aerobic stability of the same.

BACKGROUND OF THE INVENTION

The ensiling process is a method of moist forage preservation and is used all over the world. Silage accounts for more than 200 million tons of dry matter stored annually in Western Europe and the United States alone. The concept involves natural fermentation, where lactic acid bacteria ferment water soluble carbohydrates to form organic acids under anaerobic conditions. This causes a decrease in pH which then inhibits detrimental microbes so that the moist forage is preserved. The process can be characterized by four different phases.

Upon sealing in the storage unit, the first phase is aerobic, when oxygen is still present between plant particles and the pH is 6.0 to 6.5. These conditions allow for continued plant respiration, protease activity and activity of aerobic and facultative aerobic microorganisms.

The second phase is fermentation which lasts several days to several weeks after the silage becomes anaerobic. Lactic acid bacteria develop and become the primary microbial population thereby producing lactic and other organic acids, decreasing the pH to 3.8 to 5.0.

The third phase is stable with few changes occurring in the characteristics of the forage so long as air is prevented from entering the storage unit.

The final phase is feedout when the silage is ultimately unloaded and exposed to air. This results in reactivation of aerobic microorganisms, primarily yeast, molds, bacilli and acetic acid bacteria which can cause spoilage.

Aerobic instability is the primary problem in silage production. Even before storage units are open for feedout, silage can be exposed to oxygen because of management problems (i.e., poor packing or sealing). Under these types of aerobic conditions, rapid growth of yeast and mold cause silage to heat and spoil, decreasing its nutritional value.

Aerobic instability can be a problem even in inoculated silage that has undergone what would traditionally be considered a "good" fermentation phase, namely a rapid pH drop, and a low terminal pH. The yeast which contribute to instability in these conditions may be those which are tolerant of acid conditions and can metabolize the lactic acid produced by lactic acid bacteria during fermentation.

Management techniques that can be used to help prevent this condition involve using care to pack the silage well during the ensiling process and, also, using care in removing silage for feeding to minimize the aeration of the remaining silage.

The susceptibility of silage to aerobic deterioration is determined by physical, chemical, and microbiological factors. Management (compaction, unloading rates) largely effects the movement of oxygen into silage. During feedout, air can penetrate 1 to 2 m behind the silage face so that exposure to oxygen is prolonged. Fermentation acids and pH inhibit the rate of microbial growth but spoilage rates are affected also by microbial numbers and the rate of aerobic microbial growth on available substrates.

It is possible to use both chemical and biological additives in making silage to promote adequate fermentation patterns especially under sub-optimal conditions. Biological additives comprise bacterial inoculants and enzymes. Bacterial inoculants have advantages over chemical additives because they are safe, easy to use, non-corrosive to farm machinery, they do not pollute the environment and are regarded as natural products. Silage inoculants containing principally homofermentative lactic acid bacteria have become the dominant additives in many parts of the world. Their function is to promote rapid and efficient utilization of a crop's water soluble carbohydrates resulting in intensive production of lactic acid and a rapid decrease in pH. Inoculants also reduce aerobic spoilage and improve animal performance.

Several problems, however, with lactic acid bacteria inoculants have been encountered. These primarily include failure to dominate fermentation and failure to inhibit adverse microbial activity. Lactic acid bacteria inoculants have been plagued by such things as inoculants being infected by phage, inoculant strains not growing well on certain crops, technical problems associated with the lactic acid bacteria not being viable at the time of application, and of course the epiphytic lactic acid bacteria population. Because these types of homofermentative lactic acid bacteria inoculants do not always prevent or reduce undesirable microbial activity, several new approaches have been tried.

The concept of heterofermentative lactic acid bacteria in an inoculant has gained recent favor. The idea is that increased levels of undissociated volatile fatty acids, such as acetate, may inhibit other microbes that initiate aerobic deterioration. Heterofermenters have the ability to convert lactic acid to acetic acid in the presence of oxygen, and the acetate produced may inhibit other deleterious organisms. With such a mechanism, one-third of the lactic acid dry matter consumed will be lost as carbon dioxide. However a small loss of 1% or perhaps up to 2% dry matter may easily offset much larger losses by aerobic microorganisms. Concerns with heterofermentative lactic acid bacteria include effects on animal performance as well as the identification of appropriate strains useful for the procedure. Different strains of even the same species do not have identical properties and vary in their fermentation characteristics.

A review of the silage process and the use of inoculants can be found in FMS Microbiology Rev. 19 (1996) 53–68, Weinberg, ZNG., and Muck, RE, "New trends and opportunities in the development and use of inoculants for silage", the disclosure of which is incorporated herein by reference.

PCT publication WO 97/29644 discloses a single strain of *Lactobacillus buchneri* (NCIMB 40788) which was found to inhibit the growth of spoilage organisms in the storage of silage. Other attempts to identify heterofermentative organisms for silage inoculants have included (Wyss et al., 1991, "Einfluss von Luftstress und die Wirkung von spezifishen Zusatzen anf die arobe Stabilitat von Grasswelksilagen", Wirschaftseigene Futter, 37: 129–141), which used an inoculant comprising lactate and propionate producing organisms in wilted grass silage. Weinberg et al. (1995), "The effect of a propionic acid bacterial inoculant applied at ensiling, with or without lactic acid bacteria on the aerobic stability of Pearl-Millet and maize silages", *J Appl. Bacteriol*, 78:430–436 disclosed the use of *Propionibacterium shermanii* in millet, corn, sorghum, and wheat silages. Propionic acid was produced only in a wheat silage in which the pH decline wan delayed and thug aerobic stability was improved. In all other silages the pH decline was rapid and the propionic acid bacteria could not proliferate.

Another attempt included select strains of *Serratia rubidaea* and *Bacillus subtilis* along with *L. plantarum*. When used in bale grass silages the number of molds decreased significantly. Some improvement was also observed in high moisture ear corn. (Moran et al., (1993), "The development of a novel bacterial inoculant to reduce mold spoilage and improve the silage fermentation in big bale silage. *In: Silage Research* 1993, *Proceedings of the Tenth International Conference on Silage Research* (O'Kiely, P., O'Connell, M. and Murphy, J., Eds.) pp. 85–86, Dublin City University, Ireland). A similar composition to that for bale grass silage was developed for wheat silage which added Pediococcus strains to the composition. Pediococcus is capable of fermenting pentose sugars which result from hemicellulose hydrolysis in wheat silages. In a single trial with wheat silage, no improvement in the aerobic stability was observed.

The ensiling process is a complex one and involves interactions of numerous different chemical and microbiological processes. Further, different silages and different methods of ensiling present a variety of different needs. As can be seen a need exists in the art for further improvement in compositions and methods to improve the aerobic stability of silage.

It is an object of the present invention to provide a method and composition which can be used as an inoculant to improve aerobic stability of silage.

It is yet another object of the invention to provide a microorganism which can be used as a heterofermentative inoculant to decrease lactic acid content and increase acetic acid content of silage.

It is a further object of the present invention to increase dry matter recovery of silage by reducing aerobic spoilage.

It is yet another object of the invention to provide an inoculant which is safe and nonhazardous for an additive to silage.

It is a further object of the invention to provide a natural additive composition for silage.

It is yet another object of the invention to provide quality silage material as determined by temperature, pH, dry matter recovery, nitrogen profile, color and microorganism count.

Other objects of the invention will become apparent from the description of the invention which follows.

SUMMARY OF THE INVENTION

According to this invention, forage materials which are to be stored are treated with a particular strain of *Lactobacillus buchneri* to preserve forage quality and to inhibit or retard aerobic deterioration.

Thus the invention provides a method of treating forage materials to enhance their preservation which comprises administering to the forage materials an effective amount of *Lactobacillus buchneri* strain LN3957, its functional equivalents, or the forage preserving compositions produced thereby.

As explained in more detail below, the microorganism of the invention has a unique effect, different from and/or extending beyond its ability to produce volatile fatty acids, such as acetic, propionic and lactic acids, that are normally produced in fermentation. The organism produces antimicrobial factors or effects such as hydrogen peroxide which are characterized by their ability to inhibit the growth of a variety of spoilage organisms.

These substances may be isolated and purified by methods known to those of ordinary skill in the art. As such, it may be used directly to treat animal feed or silage. In other words, it may not be necessary to use a microorganism as such in the compositions and methods of this invention.

DETAILED DESCRIPTION OF THE INVENTION

Figure 1:
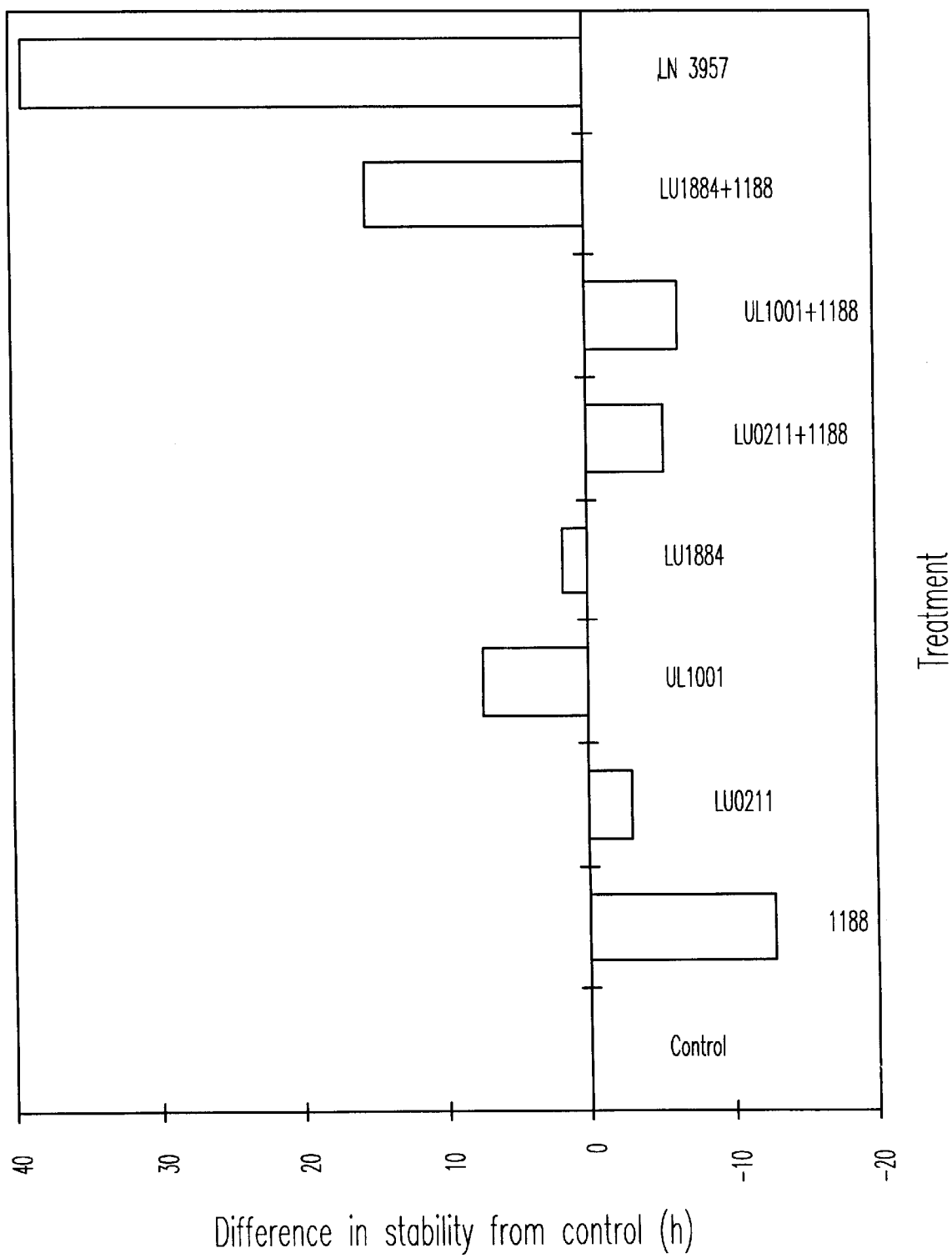
FIG. 1 is a graph depicting silage characteristics of forage treated with different treatments including the *L. buchneri* strain of the invention. (LN3957—the strain of the invention; LU1184+1188—50:50 mixture of LU1884 AND 1188; UL1001+1188—50:50 mixture of UL1001 and 1188; LU0211+1188—50:50 mixture of LU0211 and 1188; LU1884—the experimental strain of *Lb. curvatus*; UL1001—the experimental strain of *Lb. sake*; LU0211—the experimental strain of *Lb. curvatus*; 1188—the commercial product containing *Lactobacillus plantarum* LP286, LP287, LP318, LP319, LP346, and *Enterococcus faecium* SF202 and SF301; and control—uninoculated.)

According to the invention a microorganism has been isolated and purified which improves the aerobic stability of ensiled forage. A specific strain of the species *Lactobacillus buchneri* has been shown to enhance aerobic stability of silage by not only metabolizing lactic acid but also by producing a substance which is toxic to microorganisms that contribute to causing aerobic instability in silage.

In the present invention, the inhibition of organisms responsible for spoilage is accomplished by treating the silage with organisms of the species *Lactobacillus buchneri*, especially the strain *Lactobacillus buchneri* LN3957 or with compositions containing *Lactobacillus buchneri* strain LN3957 or closely related organisms, and as well by treatment with effective mutants or equivalents of *Lactobacillus buchneri* strain LN3957 and compositions containing same.

The compositions which are used in the method of the invention may be in either liquid or dry form and may contain additional bacterial strains. In solid treatment forms, the composition may comprise the *Lactobacillus buchneri* together with a carrier. The carrier may be in the nature of an aqueous or nonaqueous liquid or a solid. In solid forms, the composition may contain solid carriers or physical extenders. Examples of such solid carriers, solid diluents or physical extenders include malto-dextrin, starches, calcium carbonate, cellulose, whey, ground corn cobs, and silicone dioxide. In short, the carrier may be organic or an inorganic physical extender. The solid composition can be applied directly to the forage in the form of a light powder dusting, or if it is disbursed in a liquid carrier it can successfully be sprayed on the forage.

Typical compositions useful for treating Oilage according to this invention contain $10^2$–$10^{12}$ viable organisms/gm, preferably $10^7$–$10^{10}$ viable organisms/gm, and more preferably $10^9$–$10^{10}$ viable organisms/gm in soluble formulations. For granular formulations preferred is $10^4$–$10^{10}$ and most preferred is $10^7$–$10^8$.

The treatment range for silage is typically $10^7$–$10^{17}$ viable organisms/ton, preferably $10^9$–$10^{15}$ viable organisms/ton, and more preferably $10^{10}$–$10^{12}$ viable organisms/ton.

Those of ordinary skill in the art will know of other suitable carriers and dosage forms, or will be able to ascertain such, using routine experimentation. Further, the administration of the various compositions can be carried out using standard techniques common to those of ordinary skill in the art.

As used herein the term "strain" shall be interpreted to include any mutant or derivative of otrain LN3957 deposited with the ATCC as accession number 202118, which retains the functional activity of improving aerobic stability of forage as described and defined by the methods and examples disclosed herein. Said *Lactobacillus buchneri* LN3957 was deposited with the ATCC, 10801 University Blvd., Manassas, Va. 20110–2209, on Apr. 29, 1998.

The microorganism of the invention was purified and isolated from grass silage. After much experimentation it was discovered from testing about 4000 isolates.

After purification and isolation of the specific strain, taxonomic studies were done to identify the strain. It was identified as *Lactobacillus buchneri* and given the prototype number LN3957. According to the invention, this strain, compositions comprising this strain, or the factors produced by this strain, are used to treat forage materials.

Materials that are suitable for ensiling or storage, according to the methods of the invention, are any which are susceptible to aerobic spoilage. The material will usually contain at least 25% by weight dry matter. Such materials include rye or traditional grass, maize, including high moisture corn, whole plant corn, Lucerne, wheat, legumes, sorghum, sunflower, barley or other whole crop cereals. The silage may be in bales (a form particularly susceptible to aerobic spoilage), oxygen limiting bags, bunkers, upright stave silos, oxygen limiting silos, bags, piles or any other form of storage which may be susceptible to aerobic spoilage. Alternatively, the invention may be used with any susceptible animal feed, whether solid or liquid, e.g. for pigs, poultry or ruminants.

The activity associated with this invention may be found in other strains of *L. buchneri*, in other species of Lactobacillus, e.g. *L. kefir, L. parakefir* and *L. parabuchneri, L. brevis, L. sake, L. curvatus* and possibly also in other genera. This can be established by routine experimentation, on the basis of the information herein.

DEPOSITS

A deposit of the microorganism Lactobacillus buchneri LN3957 is and has been maintained by Pioneer Hi-Bred International, Inc., 7100 NW 62nd Avenue, Johnston, Iowa 50131–1000, since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will make available to the public without restriction a deposit of the same with the American Type Culture Collection (ATCC), Rockville, Md., 20852. The microorganism deposited with the ATCC will be taken from the same deposit maintained at Pioneer Hi-Bred and described above. Additionally, Applicant(s) will meet all the requirements of 27 C.P.R. § 1.801–1.809, including providing an indication of the viability of the sample when the deposit is made. This deposit of *Lactobacillus buchneri* LN3957 will be maintained without restriction in the ATCC Depository, which is a public depository, for a period of 30 years, or 5 years after the most recent request, or for the enforceable life of the patent, whichever is longer, and will be replaced if it ever becomes nonviable during that period.

The following examples serve to further describe and define the invention, and are not intended to limit the invention in any way.

EXAMPLES

Example 1

Buxtehude Whole Plant Corn Silage Trials

An experiment was conducted to inoculate whole plant corn forage with the heterofermentative strain LN3957 as well as bacteria that exhibit anti-yeast activity in bench-top assays, to determine whether aerobic stability of the silage is improved.

Methods

Trials were carried out by the standard methods used in European silage research studies (see Example 3). Whole plant corn (hybrid 'Noveta') was chopped and ensiled at 28.3 to 39.5% dry matter. PVC silos 4"×14" were used with 50% compaction rate (approx. 100 kg dry matter/m3) and two 48 hr periods of air infusion at 4 and 6 weeks post-ensiling. There were four locations and two replicate silos per treatment per opening day. Table 1 summarizes the treatments used.

TABLE 1

| Treatments | |
| --- | --- |
| Treatments: | Description: |
| Control | Uninoculated |
| 1188 | Commercial Product containing *Lactobacillus plantarum* LP286, LP287, LP318, LP319, LP346, and *Enterococcus faecium* SF202 and SF301 |
| LU0211 | Experimental strain of *Lb. curvatus* |
| UL1001 | Experimental strain of *Lb. sake* |
| LU1884 | Experimental strain of *Lb. curvatus* |
| LU0211 + 1188 | Mixture of LU0211 and 1188 (50:50) |
| UL1001 + 1188 | Mixture of UL1001 and 1188 (50:50) |
| LU1884 + 1188 | Mixture of LU1884 and 1188 (50:50) |
| LN3957 | The strain of the invention |

Results

Table 2 shows the pooled result of four trials and FIG. 1 is a graph depicting the results. Aerobic stability of the 'anti yeast bacteria' treated silages was similar to the untreated control silage. Silage treated with the commercial product 1188 was less stable than control silage in this study. Whole plant corn silage treated with LN3957 had 30 to 40 h higher aerobic stability than 1188 or control treatments.

TABLE 2

Treatment LSMeans -- Day 65

| TRT | pH | Stability (h) | Aerobic Loss (%) |
|---|---|---|---|
| 1188 | 4.00 | 11.13 | 12.85 |
| CONTROL | 4.02 | 24.13 | 13.62 |
| LN3957 | 3.90 | 63.25 | 8.06 |
| LU0211 | 3.98 | 21.13 | 11.92 |
| LU0211 + 1188 | 3.97 | 18.75 | 12.12 |
| LU1884 | 3.92 | 25.88 | 11.60 |
| LU1884 + 1188 | 3.94 | 39.38 | 10.96 |
| UL1001 | 3.93 | 31.38 | 9.40 |
| UL1001 + 1188 | 3.94 | 17.63 | 13.19 |

Example 2

U.S. Whole Plant Corn Silage Trials

The purpose of this trial was to look at different conditions and treatments that might affect aerobic stability of whole plant corn silage. Two different packing densities were tested along with bacterial inoculants including LN3957 and UL1001, an isolate of Lactobacillus sake which had some antiyeast activity in culture.

Methods

Trials were carried out at the Pioneer Livestock Nutrition Center (Polk City, Iowa) using Pioneer Brand Hybrid 3394. Whole plant corn was harvested and chopped at 31.9% dry matter.

Inoculation 1132 and 1174 were commercial products in soluble form. UL1001 was prepared by our contract manufacturer. LN3957 was grown and freeze-dried by Pioneer's Fermentation Lab. The treatments were solubilized and were applied on the forage with a 30cc syringe fitted with a 16 gauge needle. All treatments except propionic acid were applied at a rate of 1 ml/lb of forage for a final inoculum level of 1.0 e5 CFU/g. Propionic acid was applied at a rate of 5 ml/2.2 lb of forage. UL1001 and 1132 were combined at a 50:50 ratio.

Packing

For each treatment, 4"×14" standard PVC experimental silos were packed at our Normal (100%) packing Density [4.6 lb. (231 kg DM/m3)] or at 70% of our Normal (70%) packing Density [3.2 lb. (160 kg DM/m3].

The forage was pressed to the selected density with a hydraulic press. The silos were fitted with Fernco quick caps at each end; the top one having a Bunsen valve to allow for gas escape. After filling the silos were kept in an environmentally controlled room (approximately 72° F.) until opening.

Analyses

One pre-ensiled uninoculated forage sample and one inoculated forage sample from each treatment were taken for dry matter (DM), pH and microbial analysis. DM was determined by drying approximately 150 g of forage for 72 hours in a 55° C. oven. pH was determined after macerating 11 g of forage with 99 ml of sterile deionized water in a stomacher. Lactic acid bacteria were enumerated on modified MRS agar. Yeast and molds were enumerated on Sabouraud Dextrose (SA) agar.

On Day 11 two standard PVC silos (100% and 70% Packing Density) from each treatment were opened. Samples were taken for pH and microbial analysis.

On Day 95 three standard PVC silos (100% and 70% Packing Density) from each treatment were opened. Samples were taken for pH and lactic and acetic acid analysis. Aerobic stability was determined by placing 2.5 lb. of silage into a plastic-lined polystyrene cooler and placing a temperature probe in the center of the silage mass. The coolers were kept in a temperature controlled room. Ambient temperature and silage temperature were measured every three hours for one week and recorded by a datalogger. ROT for the silage was defined as the time in hours it took for the silage temperature to rise 1.7° C. above ambient. Average ambient temperature for this trial was 29.7° C. Cumm_DD is the integration of the area between the actual temperature curve and a line drawn at the ambient temperature. Max Temp is the maximum temperature recorded.

Treatments

| Treatments: | Description: |
|---|---|
| Control | Uninoculated |
| 1132 | Commercial Product containing *Lb. plantarum* LP286, LP287, LP329, LP346, LP347, and *E. faecium* SF202 and SF301 |
| 1174 | Commercial Product containing *Lb. plantarum* LP286, LP287, LP346, LP347, and *E. faecium* SF202 and SF301 |
| UL1001 | Experimental strain of *Lb. sake* |
| UL1001 + 1132 | Mixture of UL1001 and 1132 (50:50) |
| LN3957 | Strain of the invention |
| Positive Control | Propionic Acid |

Results and Discussion pH

Mean pH values are shown in Table 1. Day 11 values are the average of duplicate samples. Day 95 values are the average of triplicate samples. The initial pH of the forage was 5.97.

TABLE 1

Mean pH Values for Day 11 and Day 95 Silage from Two Packing Densities (PD)

| | Day 11 | | Day 95 | |
|---|---|---|---|---|
| | 100% PD | 70% PD | 100% PD | 70% PD |
| Control | 3.76 | 3.73 | 3.76 | 3.77 |
| 1132 | 3.66 | 3.66 | 3.64 | 3.67 |
| 1174 | 3.68 | 3.66 | 3.68 | 3.68 |
| UL1001 | 3.73 | 3.72 | 3.74 | 3.74 |
| 1001 + 1132 | 3.67 | 3.66 | 3.65 | 3.67 |
| LN3957 | 3.75 | 3.76 | 3.90 | 3.95 |
| Propionic Acid | 3.68 | 3.66 | 3.70 | 3.71 |

This data shows that all the treatments, including the heterofermenter LN3957, gave a good fermentation (pH<4.0). There were differences in the pH values between treatments with all packing methods. 1132 usually had the lowest pH and LN3957 had the highest pH. Packing density had no effect on pH.

Lactic and Acetic Acid

Table 2 shows the average amount of lactic and acetic acid found in the silage extracts on Day 95. The calculated lactic/acetic ratios are given in Table 3.

TABLE 2

Average Amounts of Lactic Acid and Acetic Acid Detected in Day 95 Silage (Packing density = PD)

|  | Lactic Acid (ug/ml) | | Acetic Acid (ug/ml) | |
| --- | --- | --- | --- | --- |
|  | 100% PD | 70% PD | 100% PD | 70% PD |
| Control | 1223.8 | 1124.9 | 353.8 | 400.8 |
| 1132 | 1200.4 | 1268.9 | 235.6 | 302.6 |
| 1174 | 1243.0 | 1274.9 | 282.1 | 325.7 |
| UL1001 | 1206.9 | 1220.6 | 357.0 | 444.8 |
| 1001 + 1132 | 1253.2 | 1439.4 | 267.3 | 362.6 |
| LN3957 | 739.0 | 749.2 | 900.1 | 991.5 |
| Propionic Acid | 1093.9 | 957.1 | 321.6 | 272.8 |

TABLE 3

Ratio of Lactic Acid to Acetic Acid in Day 95 silage

|  | Lactic/Acetic Ratio | |
| --- | --- | --- |
|  | 100% PD | 70% PD |
| Control | 3.5 | 2.8 |
| 1132 | 5.1 | 4.2 |
| 1174 | 4.4 | 3.9 |
| UL1001 | 3.4 | 2.7 |
| 1001 + 1132 | 4.7 | 4.0 |
| LN3957 | 0.8 | 0.8 |
| Propionic Acid | 3.4 | 3.5 |

Silage treated with LN3957 contained less lactic acid and more acetic acid, which resulted in lower lactic/acetic acid ratios than the other treatments. 1132 had the highest lactic/acetic ratio and the lowest pH.

Yeast and Mold Counts

Tables 4 and 5 show Day 11 yeast and mold counts. On Day 11 LN3957 and Propionic Acid had lower yeast and mold counts than the other treatments.

TABLE 4

Yeast CFU/g (wet matter basis) Packing Density = PD

|  | Day 0 | Day 11 | |
| --- | --- | --- | --- |
|  | 100% PD | 100% PD | 70% PD |
| Control | 1.85E+06 | 2.20E+05 | 3.20E+05 |
| 1132 | 3.40E+06 | 4.68E+05 | 2.04E+06 |
| 1174 | 4.40E+06 | 3.13E+05 | 5.15E+05 |
| UL1001 | 4.45E+06 | 5.30E+05 | 3.72E+05 |
| 1001 + 1132 | 4.65E+06 | 2.78E+05 | 1.68E+05 |
| LN3957 | 7.95E+06 | 1.96E+05 | 5.89E+04 |
| Propionic Acid | 2.15E+06 | 1.48E+05 | 6.71E+04 |

TABLE 5

Mold CFU/g (wet matter basis) Packing Density = PD

|  | Day 0 | Day 11 | |
| --- | --- | --- | --- |
|  | 100% PD | 100% PD | 70% PD |
| Control | 1.65E+06 | 1.25E+03 | 1.04E+03 |
| 1132 | 1.10E+06 | 9.33E+03 | 3.46E+03 |
| 1174 | 6.00E+05 | 2.64E+03 | 6.50E+02 |
| UL1001 | 5.50E+05 | 2.75E+03 | 3.32E+03 |
| 1001 + 1132 | 5.50E+05 | 2.37E+03 | 3.05E+03 |
| LN3957 | 3.00E+05 | 3.00E+01 | <E+02 |
| Propionic Acid | 2.00E+05 | <E+02 | <E+02 |

Aerobic Stability

Average values for the 3 measures of aerobic stability—ROT, Cumm_DD and Max Temp—are given in Table 6.

TABLE 6

Average ROT, Cumm_DD and Max Temp Values

|  | ROT | | Cumm_DD | | Max Temp | |
| --- | --- | --- | --- | --- | --- | --- |
|  | 100% Packing Density | 70% Packing Density | 100% Packing Density | 70% Packing Density | 100% Packing Density | 70% Packing Density |
| Control | 32 | 28 | 138.8 | 86.4 | 37.6 | 34.5 |
| 1132 | 26 | 34 | 117.6 | 80.2 | 36.7 | 34.6 |
| 1174 | 28 | 28 | 139.3 | 130.5 | 38.6 | 39.3 |
| UL1001 | 32 | 30 | 89.9 | 54.0 | 34.9 | 33.2 |
| 1001 + 1132 | 30 | 28 | 107.0 | 55.4 | 36.2 | 33.7 |
| LN3957 | 56 | 90 | 57.6 | 59.9 | 33.9 | 35.9 |
| Propionic Acid | 42 | 28 | 102.2 | 76.7 | 35.9 | 35.9 |

At both packing densities, LN3957 inoculated silages had the best (highest) ROT values; except for LN3957 (at 70% packing density) all ROT values were less than 75 hours.

LN3957 treated silage had the lowest CUMDD and Max Temp values at 100% packing density, and lower CUMMDD than control, 1174 and 1132 treated silage at 70% density.

TABLE 7

Yeast CFU/g (wet matter basis) in Silage After Exposure to Air

|  | Time After Exposure to Air | | | |
| --- | --- | --- | --- | --- |
|  | 0 Hrs. | 24 Hrs. | 48 Hrs. | 93 Hrs. |
| Control | 5.36E+04 | 2.56E+07 | 5.70E+08 | 1.13E+09 |
| 1132 | 6.08E+04 | 8.85E+06 | 2.55E+07 | 7.86E+08 |
| UL1001 | 4.73E+04 | 1.63E.07 | 1.35E+07 | 4.77E+08 |
| LN3957 | nd | 5.00E.03 | 5.55E.06 | 6.14E+07 |
| Propionic Acid | 4.95E+02 | 7.56E+03 | 1.67E+06 | 8.54E+07 |

Table 7 shows that silage treated with LN3957 and propionic acid had lower yeast populations 24–93 hr after exposure to air than control silage or silage treated with 1132 or UL1001.

Example 3

Protocol for Determining Aerobic Stability

DETERMINATION OF AEROBIC DETERIORATION SYSTEM VÖLKENRODE

H. Honig

The system is based on the linear correlation existing between temperature rise and intensity of $CO_2$-production, which again can be transformed into DM-(Glucose-) losses via the respiration formula. The conversion factors given later relate to the test set-up used here. Higher insulation and larger forage amounts will give higher temperature rise at the same losses.

Containers:

1 l aluminum tins, 100 mm diameter, 150 mm high, covered with plastic sheet, 10 mm diameter hole in tin bottom and covering sheet, 60 mm styrofoam insulation to the sides, 30 mm to top and bottom.

Gas flow:

Gas flow is secured by the difference in specific weight of the $CO_2$, produced during the process, and the surrounding air. The hole diameter is sufficient for the necessary gag exchange as is shown by comparative measurements with the "Sapromat-system" (Compensating the $O_2$ deficit automatically at demand). Tin cover should be plastic to avoid excessive drying of the surface layers of material.

Temperature measurement:

Thermo couple connected to a 100 channel automatic printer. Measurements are taken at 6-hour intervals and averaged daily.

Basic temperature:

Containers are stored in a 20° C. controlled temperature room. If material is colder at the beginning, it should be given time to adjust to 20° C. before applying insulation.

Filling quantity:

100 g of DM is the basic filling quantity. As temperature rise shows a linear correlation to filling quantity in a range from 60 to 130 g DM, data can be corrected for small deviations. If material with high bulk density does not fill the 1 l volume, styrofoam disks with a center hole of 12 mm are put in as a substitute.

Loss calculation

DM content is the second factor besides filling quantity to be allowed for in the conversion from temperature rise to DM losses. The following table is based on extensive comparisons of temperature rise in the described set-up and simultaneous $CO_2$ determinations.

Dm loss, % per day at 1° C. temperature rise a) Factor $F_{DM100}$ (at 100 g DM filling weight)

b) Factor $F_{DM}$ (at variable filling weight (60 . . . 130 g))

$$F_{DM} = F_{DM100} \times \frac{100}{DM \text{ filling weight}(g)}$$

Loss curve:

The daily determined losses are accumulated and plotted versus storage time. Normal storage time in Völkenrode is 9 days.

What is claimed is:

1. A composition for use as a silage inoculant comprising: a silage quality preserving amount of *Lactobacillus buchneri* LN3957 or a mutant thereof which retains the silage preservative activity of *Lactobacillus buchneri* LN3957, and carrier.

2. The composition of claim 1 wherein the composition contains from about $10^2$ to about $10^{12}$ viable organisms per gram wet weight of silage.

3. The composition of claim 1 wherein the composition contains from about $10^7$ to about $10^{10}$ viable organisms per gram wet weight of silage.

4. The composition of claim 1 wherein the composition contains from about $10^9$ to about $10^{10}$ viable organisms per gram wet weight of silage.

5. The composition of claim 1 wherein the carrier is liquid.

6. The composition of claim 1 wherein the carrier is solid.

7. The composition of claim 1 wherein said carrier is a solid carrier selected from the group consisting of calcium carbonate, starch, and cellulose.

8. A biologically pure culture of *Lactobacillus buchneri*, strain LN3957, having ATCC accession number 202118.

9. A method for treating silage by inhibiting the growth thereon of spoilage organisms selected from yeasts, molds and spore-forming bacteria, which comprises: adding to said silage a spoilage organism inhibiting amount of the composition of claim 1.

10. A method for treating silage, which comprises adding thereto a microorganism as defined in claim 1.

11. A method according to claim 9, wherein the silage is grass.

12. A method according to claim 9, wherein the silage is maize.

13. A method according to claim 9, wherein the silage is alfalfa.

14. A method according to claim 9, wherein the silage is wheat.

15. A method according to claim 9, wherein the silage is legumes.

16. A method according to claim 9, wherein the silage is sorghum.

| % DM | 0 | 1 | 2 | 3 | 4 | 5 | 6 | 7 | 8 | 9 |
|---|---|---|---|---|---|---|---|---|---|---|
| 10 | 0.450 | 0.438 | 0.425 | 0.413 | 0.400 | 0.388 | 0.375 | 0.363 | 0.350 | 0.338 |
| 20 | 0.325 | 0.315 | 0.306 | 0.279 | 0.287 | 0.278 | 0.268 | 0.259 | 0.249 | 0.240 |
| 30 | 0.230 | 0.226 | 0.222 | 0.218 | 0.214 | 0.210 | 0.206 | 0.202 | 0.198 | 0.194 |
| 40 | 0.190 | 0.186 | 0.181 | 0.177 | 0.172 | 0.168 | 0.163 | 0.159 | 0.154 | 0.150 |
| 50 | 0.145 | 0.140 | 0.136 | 0.131 | 0.127 | 0.123 | 0.118 | 0.114 | 0.109 | 0.105 |
| 60 | 0.100 | | | | | | | | | |

17. A method according to claim 1, wherein the silage is sunflower.

18. A method according to claim 9, wherein the silage is barley.

19. A method according to claim 9, wherein said composition is added upon storage of said silage.

20. A method according to claim 9, which comprises storing the treated silage for at least 30 days.

21. A method according to claim 9, wherein the silage is in a bale.

22. A method according to claim 9, wherein the silage is in a bag.

23. A method according to claim 9, wherein the silage is in a bunker.

24. A method according to claim 9, wherein the silage is in a stave silo.

25. A method according to claim 9, wheiein the silage is in a silo.

26. A method according to claim 9, wherein the silage is in bags.

27. A method according to claim 9, which comprises adding to the silage a silage quality preserving amount of *Lactobacillus buchneri* strain LN3957, having ATCC Accession Number 202118.

28. Silage comprising a silage quality preserving amount of *Lactobacillus buchneri* LN3957 or a silage quality preserving amount of a mutant thereof.

29. The method of claim 9, wherein said silage is a component of animal feed.

* * * * *